United States Patent [19]
Dunseath, Jr.

[11] Patent Number: 4,763,659
[45] Date of Patent: Aug. 16, 1988

[54] DRY ELECTRODE SYSTEM FOR DETECTION OF BIOPOTENTIALS

[75] Inventor: W. J. Ross Dunseath, Jr., Durham, N.C.

[73] Assignee: Spring Creek Institute, Inc., Durham, N.C.

[21] Appl. No.: 898,235

[22] Filed: Aug. 20, 1986

Related U.S. Application Data

[63] Continuation-in-part of Ser. No. 767,963, Aug. 21, 1985, Pat. No. 4,669,479.

[51] Int. Cl.$^4$ ................................................. A61B 5/04
[52] U.S. Cl. .................................... 128/640; 128/644; 128/696; 128/902
[58] Field of Search ................................. 128/639–641, 128/643, 644, 696, 902, 798, 802, 803

[56]         References Cited
         U.S. PATENT DOCUMENTS

| | | | |
|---|---|---|---|
| 3,500,823 | 3/1970 | Richardson et al. | 128/639 |
| 3,565,060 | 2/1971 | Sipple | 128/696 |
| 3,586,991 | 6/1971 | Vosteen | 330/207 P |
| 3,605,728 | 9/1971 | Ogle | 128/696 |
| 3,620,208 | 11/1971 | Higley et al. | 128/639 |
| 3,628,527 | 12/1971 | West | 128/639 |
| 3,679,989 | 7/1972 | Thibodeau | 330/185 |
| 3,744,482 | 7/1973 | Kaufman et al. | 128/639 |
| 3,880,146 | 4/1975 | Everett et al. | 128/710 |
| 4,051,842 | 10/1977 | Hazel et al. | 128/640 |
| 4,088,133 | 5/1978 | Twentier | 128/303.13 |
| 4,200,109 | 4/1980 | McMorrow, Jr. | 128/696 |
| 4,235,241 | 11/1980 | Tabuchi et al. | 128/639 |
| 4,243,044 | 1/1981 | Blancke | 128/696 |
| 4,300,575 | 11/1981 | Wilson | 128/79 B |
| 4,352,359 | 10/1982 | Larimore et al. | 128/640 |
| 4,353,372 | 10/1982 | Ayer | 128/640 |
| 4,365,634 | 12/1982 | Bare et al. | 128/640 |
| 4,458,696 | 7/1984 | Larimore | 128/640 |
| 4,492,932 | 1/1985 | Rusznyak | 330/292 |

FOREIGN PATENT DOCUMENTS

| | | | |
|---|---|---|---|
| 0000759 | 2/1979 | European Pat. Off. | 128/640 |
| 2735050 | 2/1979 | Fed. Rep. of Germany | 128/640 |
| 85/00017 | 1/1985 | World Int. Prop. O. | 128/640 |
| 684713 | 9/1979 | U.S.S.R. | |

OTHER PUBLICATIONS

Rositano et al., "Ultra-Soft Dry Electrodes . . ." Med. Inst., vol. 7, #1, Jan. Feb. 1973, p. 76.
Betts et al., "Method for Recording ecgs . . ." Med. & Biol. Eng., vol. 14, No. 3, pp. 313–315, May 1976.

Primary Examiner—Lee S. Cohen
Attorney, Agent, or Firm—Oblon, Fisher, Spivak, McClelland & Maier

[57]          ABSTRACT

A dry electrode system for the detection of biopotentials existing on the surface of the skin of a living body, including a dry electrode pad with a resilient conductive pad adhering to at least one adhesive pad or otherwise opposed adhesive surfaces, one of which is adapted to engage the skin of the living body. The dry electrode pad makes electrical connection to an amplifying circuit which transmits a biopotential derived from the conductive pad to a monitor. The amplifying circuit includes a conductive input contact for making electrical contact to the conductive pad, a lead amplifier having an input coupled to the input contact, and a voltage driven shield coupled to the output of the lead amplifier and surrounding portions of the input contact not in engagement with the dry electrode pad. In a preferred embodiment, conductive adhesive layers are applied to opposed sides of a conductive foam pad to construct the dry electrode pad.

74 Claims, 7 Drawing Sheets

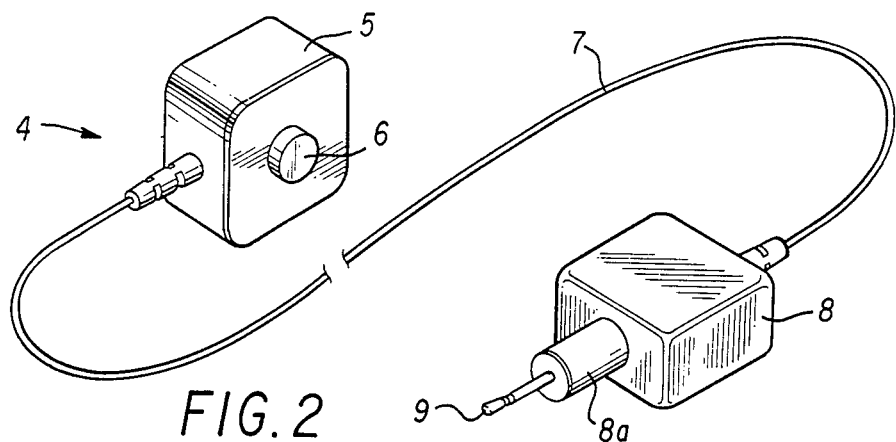
FIG. 2
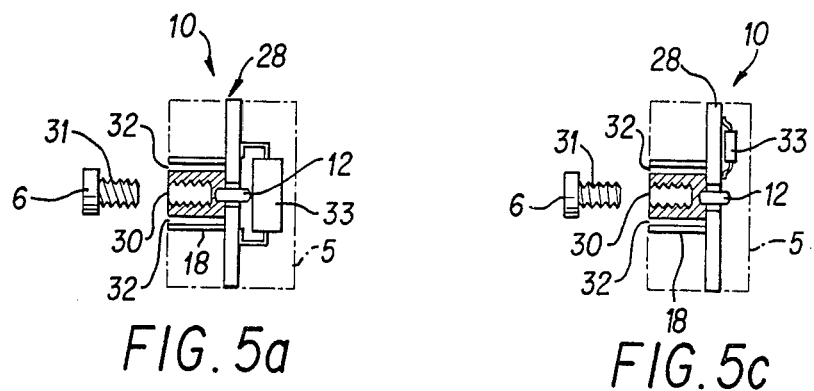
FIG. 5a
FIG. 5c
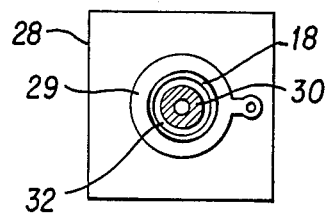
FIG. 5b
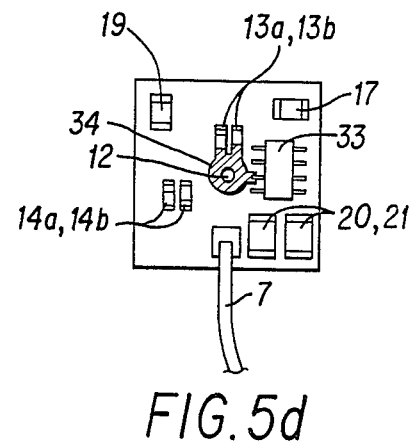
FIG. 5d

DRY ELECTRODE SYSTEM FOR DETECTION OF BIOPOTENTIALS

This is a continuation-in-part of co-pending application Ser. No. 767,963 filed on Aug. 21, 1985, now U.S. Pat. No. 4,669,479.

BACKGROUND OF THE INVENTION

1. Field of the Invention

The invention described herein pertains to the detection of potentials existing on the surface of the skin of the living body, which potentials are generated by various sources such as muscle or nervous system activity within the body.

2. Discussion of the Background

Present biopotential detection techniques typically involve the use of conductive pastes or gels in combination with a metallic contact surface to form an electrode capable of transforming ionic current flow in the body into electronic current flow in the measuring apparatus. There are several realizations of this basic type of electrode, and all of them suffer from the various disadvantages of wet systems, such as skin irritation, loss of electrical contact due to drying paste or lead wires falling off, poor shelf life, etc. Attempts have been made to eliminate the pastes and gels in two separate ways: the introduction of new electrode materials, and the incorporation of amplifier electronics into the electrode itself.

The materials introduced in the prior art as dry electrodes generally have not been accepted in the medical field due to poor performance. For example, most of the metals and conductive composite materials such as those disclosed in U.S. Pat. Nos. 3,56,860 and 3,606,881, generate excessive low frequency electrical noise voltages when in contact with a saline solution such as the human sweat which invariably collects on the surface of the skin beneath the electrode, but there is little or no attention given to this problem in the prior art. Furthermore, many of these materials are too stiff to conform to irregularities in skin surface, thus resulting in an unstable dry skin contact subject to excessive movement artifact.

Another group of efforts to obtain disposable electrodes has sought to modify conventional non-conductive pressure-sensitive adhesives by loading them with fine conductive particles such as carbon powder (U.S. Pat. No. 3,911,906) or metal-coated plastic microspheres (U.S. Pat. No. 3,566,059). However, the conductive filler materials have tended to degrade the adhesives, requiring the electrode pad to be undesirably large if it is to adhere adequately to skin. In U.S. Pat. No. 3,911,906, for example, the preferred diameter of the adhesive pad is two inches, not to be greatly reduced, but such a large area electrode detects signals from a large volume of tissue, which is not always desirable especially if the signal of interest is from a source distant from the electrode site. In this case, the increased level of electrical activity from the muscles directly below the electrode would result in excessive interference or artifact in the recording. Second and more fundamental, conductive adhesives of this type in contact with unprepared dry skin generally do not establish sufficient electrical conduction to the body to be of particular use with present monitoring technology.

Another group of "dry" electrode materials includes a variety of conductive gums or gels which are sufficiently viscous to form the main body of a disposable electrode while simultaneously providing both its adhesion and its electrical connection to the skin. Hydrogels such as those disclosed in U.S. Pat. Nos. 3,998,215; 4,391,278; and 4,515,162 cannot truly be regarded as "dry" materials since by definition their water and/or alcohol content is typically high (for example, 30-75% by weight for U.S. Pat. No. 4,391,278). This leads to problems of electrode dryout, special packaging, and poor shelf life. A group of materials more satisfactory in this respect has been derived from polysaccharides such as gum karaya. For example, U.S. Pat. Nos. 4,125,110 and 4,229,231 describe karaya-based conductive-adhesive gels of relatively low water content for use in disposable ECG electrodes. As pointed out in U.S. Pat. No. 4,273,135, however, the variable conditions of growth and processing of these naturally occuring polymers can lead to corresponding inconsistency in the physical and chemical properties of the resulting gels. Furthermore, steps must be taken to control problems of microbial growth and skin irritation that these organic materials could otherwise engender. Consequently, synthetic polymer gels have been developed that can more consistently provide the necessary physical properties. Examples of such materials are described in U.S. Pat. Nos. 4,273,135 and 4,554,924.

Both the natural and the synthetic gels are now being used as "essentially dry" disposable electrodes (cf. U.S. Pat. No. 4,554,924 for an example). Although such electrodes represent an improvement over earlier "dry" disposables, they still suffer from limitations similar to those of the modified pressure sensitive adhesives, namely, poor skin adhesion, especially in hair and sweat, and low conductivity on unprepared dry skin. In addition, the junction between the alligator-clip lead and the foil backing of the electrode is susceptible to mechanical instability, making it a significant source of electrical interference, particularly if the lead wires are subject to movement. Finally, these gel-foil disposable electrodes remain far more costly than the reusable wet electrode technology that is still most widely used for resting or diagnostic ECG procedures. All these limitations are sharply reduced by the novel dry-electrode technology according to the present invention to be described subsequently.

Another approach to realizing a dry electrode, placing an electronic amplifier on the electrode, is based on the idea that a high impedance amplifier is able to detect a signal from a high impedance source with a minimum of signal distortion, and then drive the signal through a long cable with a minimum of interference by virtue of the low output impedance of the amplifier. One problem is that many previously disclosed designs, including DC biased transistor amplifiers, differential amplifiers, and amplifiers with gains above unity are not compatible with commonly used monitoring equipment unless some adjustment or modification is made to the monitor. Even unity-gain, DC-biased transistor amplifiers that are capacitively coupled at the output cannot conveniently be used with different types of monitors without the risk of frequency distortion caused by impedance mismatching to the different monitor inputs, and without large transient DC offsets arising when switching leads.

Another problem has been questionable reliability, as demonstrated by a group of devices utilizing a capacitively coupled input to an amplifier constructed on a metallic electrode coated with a dielectric. This type of electrode is prone to failure from dielectric breakdown due to scratches or high voltages, and exhibits undue sensitivity to external electrostatic fields.

A group of amplifiers using bipolar integrated circuit operational amplifiers with unity gain has been disclosed, but a means for adequately protecting the electronic circuitry from repeated exposure to high voltages, without compromising the essential electrical characteristics of the amplifier input, has not been demonstrated. Defibrillation voltages, static charge accumulation on the skin and clothes, and other medical equipment may cause potentials greater than 25,000 volts to contact the input to the electrode amplifier on a repeated basis, resulting in permanent failure of the device if not protected. The prior art shows the use of input resistors or unspecified current limiters for device and patient protection, but fails to show a means for compensating for the degradation of input impedance to the device as a result of parasitic capacitance coupling to ground through the resistor or current limiter. Furthermore, a single input resistor or current limiter may not provide adequate protection for some types of integrated circuit amplifiers such as CMOS devices which are sensitive to large input voltages rather than currents. Additionally, there previously has been no disclosure of a means for incorporating very small batteries into the amplifier or lead wire in order to continuously power the amplifier for a period of more than a year without prematurely exhausting the batteries. Due to excessive current demand by the amplifier, especially when the input is unconnected and the output has drifted to saturation as a result, it has previously been necessary to disconnect the batteries from the amplifier when not in use, either by physical removal or by means of a power switch, thus adding undesirable complexity to the operation of the electrode lead wire.

SUMMARY OF THE INVENTION

Accordingly, it is an object of the present invention to provide a new and improved dry electrode system for detecting potentials on the skin of a living body without the use of conductive pastes or gels under conditions ranging from dry to sweat-soaked skin.

A further object of this invention to provide a novel dry electrode system which is immune from destruction or instability caused by repeated exposure to high voltages over long time periods.

Yet another object of this invention is to provide a novel dry electrode system capable of providing a signal to conventional monitoring devices without the need for adjustment or modification to the monitor.

These and other objects are achieved according to the invention by providing a novel dry electrode system for the detection of biopotentials existing on the skin of a living body, which biopotentials arise from generators within the body such as heart, muscle or nervous system activity, including a dry electrode pad formed of a resilient conductive pad having a dry conductive center and adhesive means for adhering the dry electrode pad to the skin and to a conductive contact. The conductive contact is coupled to the input of a lead amplifier having an output which is connected to a shield surrounding portions of the contact such that the shield is voltage driven by the output of the lead amplifier. The lead amplifier is attached to one end of a shielded multi-conductor lead cable which provides bipolar power supply voltages, common potential, and an output conductor to the lead amplifier. At the other end of the lead cable is provided a battery pack which in turn is connected to a lead wire connector suitable for interfacing with a monitor.

Through suitable enhancements of the electrical properties of the reusable components of the system—i.e., the leads—substantial improvements in the cost/performance characteristics of the disposable portion—i.e., the electrode pads—can be obtained. In particular, incorporation of active amplifiers in the leads allows for an increase in the impedance of the skin-to-electrode contact, and thus permits use of a wider range of materials for the disposable pads than would be suitable for use with conventional passive leads.

According to one embodiment of the invention, the conductive pad is mounted on an apertured insulative adhesive pad which has one adhesive surface adapted to adhere to the skin and an opposite adhesive surface adhering to the lead amplifier housing (or case). Alternatively, the conductive pad is sandwiched between opposed apertured non-conductive adhesive pads.

In another embodiment, the opposed sides of the conductive pad are coated, except for central portions of the opposed sides, with respective adhesive coatings, the central portions being uncoated in order so as not to impede signal transmission.

In another embodiment, one side of the conductive pad is coated with a conductive adhesive adapted to adhere to the skin, and the opposite side of the conductive pad is coated, except for the central portion, with a non-conductive adhesive for adhering to the lead amplifier case. In a preferred embodiment, both sides of the conductive pad are coated with suitable conductive adhesives.

The conductive pad is made of a resilient conductive material and with the adhesive makes electrical contact with the skin, yet prohibits direct physical contact to the skin by the lead amplifier and contact. This inhibits disease transmission, since the pad is disposable, and enables reuse of the lead amplifier and associated lead wire.

In a preferred embodiment, the lead amplifier is mounted in a small plastic case with the shielded electrical contact extending from the case. Additionally, the multi-conductor lead cable also is surrounded by a conductive shield which is either driven by a voltage follower amplifier connected to the output of the lead amplifier, or otherwise connected to common potential. Additionally, the lead amplifier has its input protected by a diode circuit which shunts bipolar currents to power supply common thereby to protect the high input impedance lead amplifier from high amplitude voltage sources. This diode circuit also provides a means for minimizing electrical power required by the lead amplifier, which enables the use of a miniature battery pack at the opposite end of the lead wire cable to power the lead amplifier continuously for long time periods.

The voltage-driven shield surrounds the input contact and an input resistor connecting the contact to the lead amplifier, and serves to maintain a high input impedance into the lead amplifier while shielding the input from external electric interference.

Dry ground contact for referencing the lead amplifier common potential to the body is implemented through a passive lead wire termination in combination with a disposable conductive pad on the skin. The pad may be held in contact with the skin by means of an elastic strap or adhesive.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 is a perspective view of the inventive lead wire with lead amplifier housing and one embodiment of the battery housing and lead wire connector;

FIGS. 5a and 5b are schematic side and plan views, respectively, illustrating details of the physical geometry of an embodiment of the lead amplifier circuit board and driven shield, using a dual-in-line integrated circuit package;

FIGS. 5c and 5d are respectively schematic side and plan views illustrating another embodiment of the lead amplifier circuit board and driven shield using a surface mount integrated circuit package and components;

DESCRIPTION OF THE PREFERRED EMBODIMENTS

Figure 1A:
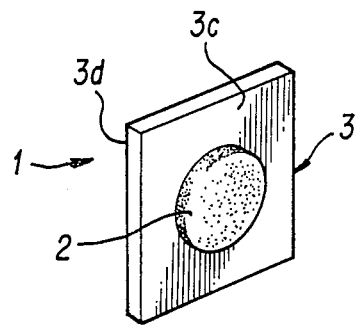
FIGS. 1a and 1b are perspective views of opposite sides of one embodiment of the dry electrode pad with a conductive pad center according to the invention.
Figure 1B:
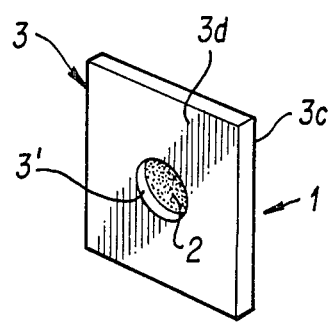

Referring now to the drawings, wherein like reference numerals designate identical or corresponding parts throughout the several views, and more particularly to FIGS. 1a–1g thereof, an embodiment of the dry electrode pad 1 of the present invention is shown. As shown in FIGS. 1a and 1b, the dry electrode pad 1 of the invention includes a resilient conductive pad 2 and an insulative adhesive pad 3. The conductive pad 2 is mounted over an aperture 3' formed is the center of the adhesive pad 3. The conductive pad 2 is a material with three essential traits: resiliency, electrical conductivity, and electrical stability. The material must be flexible in order to conform to a body surface contour yet possess a sufficient resiliency to maintain intimate contact with the skin despite dynamic variations in contour, for example die to breathing or similar bodily movement. Thus, the resiliency of the material forming the conductive pad 2 as measured by the Ball Rebound test (ASTM Designation D 3574-81) must exceed 5% and preferably be as high as 20%. If the conductive pad 2 itself contacts the skin, it is furthermore essential that the material establish an AC electrical impedance to dry skin of not more than 1.5 million ohms at a frequency of 10 Hz. (If conductive pad 2 is part of a composite dry electrode pad and does not itself contact the skin, then it is only essential that the composite dry electrode pad establish the stated A.C. impedance to dry skin.) Finally, the material of the conductive pad 2 must maintain an electrical stability in terms of self-generated AC noise voltages over a bandwidth of 0.15 Hz to 100 Hz (which is the COMBINED OFFSET INSTABILITY and INTERNAL NOISE requirement of the AAMI standard for ECG disposable eectrodes), under conditions ranging from dry to saturation with a 0.9% saline solution. The maximum acceptable AC noise voltage is 150 microvolts peak value, although it is preferable to maintain noise voltages well below this value. Additionally the material must maintain a stable DC voltage of less than 100 mV under dry to 0.9% saline saturation conditions.

One material capable of meeting the above restrictions is low density, carbon loaded polyurethane foam, but it is understood that any material meeting the above specifications falls within the scope of the invention. If the material is a flexible open-cell foam, such as conductive polyurethane (Type 1 foam manufactured by Conductive Materials, Inc., San Jose, Calif., for example), an enhancement in electrode performance may be realized by coating or forming on the skin-side surface of the foam a thin, flexible, smooth coating or layer of curable conductive material meeting the conductivity and electrical stability restrictions outlined above, with the intent of maximizing the dry conductive contact area to the skin while maintaining the mechanical properties of the conductive pad as previously outlined. One example of such a surface is realized by mixing one and one half parts by volume graphite powder (−300 mesh, 99.5% pure) with five parts by volume distilled water and ten parts by volume liquid latex. A thin layer of this mixture is spread on a smooth glass surface and the conductive foam of 400 ohm-cm resistivity is held in contact with the mixture until it cures, resulting in a smooth conductive skin adhering so the surface of the foam. According to the invention, a conductive layer can also be formed on the opposite side of the conductive pad to achieve a further enhancement in electrode performance and to simplify use in the field.

Alternatively, a closed-cell conductive foam such as a crosslinked, vinyl-nitrile polymer is acceptable if it meets the above restrictions for the conductive pad. This material has an additional advantage in that a sealed-surface skin may be formed on the surface of the foam, thus increasing the area of contact to the body. The sealed-surface skin is an integral part of the foam as opposed to the open-celled foams, which must have a separate surface added later in the manufacturing process. An example of an acceptable closed-cell foam is Type CIC foam manufactured by Uniroyal, Inc., Mishawaka, Ind.

The dry electrode pad 1 as shown in FIGS. 1a–1d includes a compliant adhesive pad 3 made of a material such as cross-linked polyethylene foam. Adhesive pad 3 serves to hold the conductive pad 2 in contact with the skin while holding conductive pad 2 in contact with a conductive contact 6 discussed hereinafter. To this end, the skin-side 3c of the adhesive pad 3 is coated with a pressure sensitive hypoallergenic medical adhesive providing a tacky skin-engaging surface, while the lead-side 3d of the adhesive pad 3 is coated with a pressure sensitive removable adhesive of reduced tackiness to engage the lead. It is important that the lead-side adhesive is fully removable, i.e., it leaves no residue on the lead after removal in order to avoid contamination and disease transmission. One example of a suitable medical adhesive is Type MA-23 adhesive manufactured by Adhesives Research Inc., Glen Rock, PA. An example of a suitable removable adhesive is Type AS-23 acrylic based adhesive, also manufactured by Adhesives Research, Inc.

Figure 1C:
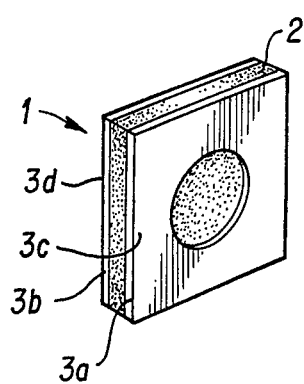
FIGS. 1c and 1d are perspective views of opposite sides of a second embodiment of the dry electrode pad of the invention.
Figure 1D:
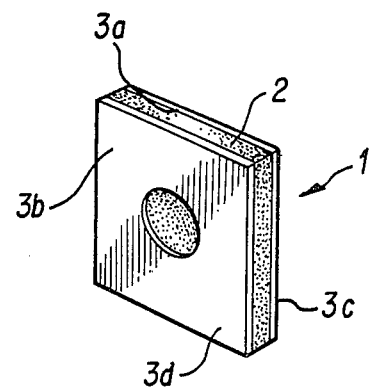

In the embodiment shown in FIGS. 1a and 1b, the dry electrode pad 1 includes a single insulative adhesive pad 3 with a central aperture of slightly smaller diameter than the diameter of the conductive pad 2 while holding it firmly in place against the skin. Another embodiment of the adhesive pad, illustrated in FIGS. 1c and 1d, is a single conductive pad 2 with thin insulative adhesive pads 3a and 3b mounted on both sides with central apertures to allow electrical contact to skin and a lead contact. As in FIG. 1a, the adhesives are of medical quality on the skin-side 3c and removable quality on the lead-side 3d.

Figure 1E:
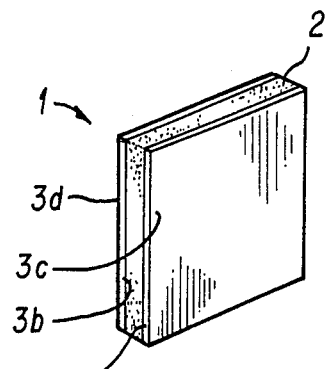
FIGS. 1e and 1f are perspective views of opposite sides of a third embodiment of the dry electrode pad according to the invention.

In another embodiment of the electrode pad, the skin-side adhesive 3c in FIG. 1e is a conductive adhesive covering most, if not all of the surface of conductive pad 2. The conductive adhesive must fulfill both the electrical and adhesive requirements stated above for skin-side components of the adhesive pad. That is, it must be a hypoallergenic medical adhesive providing a tacky, conductive and skin-engaging surface. In addition, the combination of the conductive adhesive and foam pad substrate must meet the impedance and noise baseline restrictions outlined above for conductive pads. If the characteristics of the conductive adhesive and foam pad 2 preclude direct lamination of adhesive to foam, a tissue substrate 3 coated on both sides 3a and 3c may be used as a manufacturing aid. Several combinations of foam and adhesive allow for the lamination of the conductive adhesive directly to foam, and may be used within the restrictions given above for this embodiment of the electrode pad. In such cases, the tissue substrate 3 is eliminated, and 3a and 3c become the surfaces of a single layer of conductive adhesive. The lead-side shown in FIG. 1f remains the same regardless of the type of foam used, and has the same configuration as described for the embodiment of FIG. 1d.

Figure 1F:
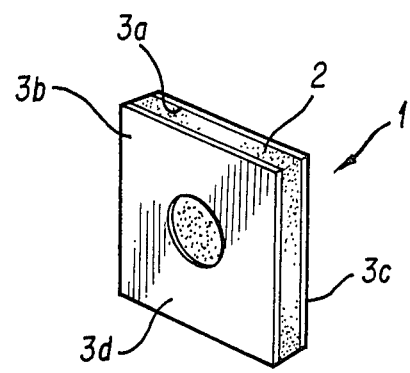
Figure 1G:
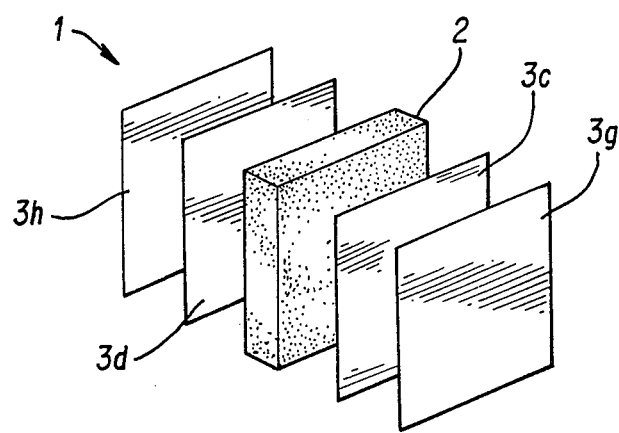
FIG. 1g is a perspective view of the preferred embodiment of the dry electrode pad of the invention.

A preferred embodiment of the adhesive pad is shown in FIG. 1g. In this example, conductive pad 2 is coated on most, if not all of the surface of each of its sides with a conductive adhesive meeting the requirements listed above for conductive adhesives. In addition, the lead-side adhesive must remove from the lead connector and lead amplifier housing without leaving a residue. The resulting foam/conductive adhesive electrode pad must meet the impedance and noise baseline requirements given previously for conductive pads. If the surface characteristics of foam pad 2 preclude direct lamination of conductive adhesive to foam, than 3c and 3d represent tissue substrates coated with conductive adhesive for use as manufacturing aids. The preferred thickness of the foam substrate for this embodiment is 0.125 inches, although a range of from 0.06 to 0.5 inches is acceptable. It is desirable to have the conductive adhesive meet all the restrictions for both skin-side and lead-side adhesives in order to eliminate the distinction between the sides of the pad, thus simplifying its use. In order to protect the adhesives during storage, release liners 3g and 3h in FIG. 1g cover the electrode pad. Various methods of quick release of the liners are contemplated, including tabs extending from the edge of the liner, or corners cut from the edge of the electrode pad without a corresponding cut on the liner, etc.

With the extended range of contact impedance to the body (1.5 million ohms @ 10 Hz) now allowed through the use of the high impedance lead amplifier of the invention several adhesives with satisfactory combinations of adhesive and electrical characteristics are readily obtained. For example, several generic medical-grade pressure-sensitive adhesives have been modified to provide adequate conductivity without seriously degrading their adhesive properties. In determining the acceptability of the following adhesive/foam constructions, several parameters are observed. These include contact impedance to the body at 10 Hz (measured with a 100 pA RMS test current), and DC voltage offset and AC (0.15 to 100 Hz) noise baseline of two pads mated face-to-face with an intervening tissue soaked in 0.9% saline solution. The preferred embodiment of the electrode pad is used in all cases, with a conductive silicon rubber material of less than 100 ohm-cm resistivity used as the electrical contact to the lead-side of the pads. The adhesive characteristics examined include adhesive strength to the conductive rubber contacts and adhesive residue remaining on the rubber surface after release. The test was also applied to representative insulative lead housing materials such as polypropylene. Testing adhesive characteristics vs. skin proved to be more difficult since the various standards proposed by agencies such as the ASTM and Pressure-Sensitive Tape Council have been shown in tests by UBTL/FDA to be extremely poor predictors of actual performance on skin. In practice, therefore, the only pertinent test of adhesion is the empirically determined ability to remain attached to human skin under an adequate variety of test conditions and skin types. The following examples of conductive adhesives all exhibit acceptable adhesive characteristics, including sufficient adhesive strength to skin, conductive rubber and insulative plastic, with little or no residue left on these surfaces after release. The electrical properties meet the requirements listed previously and are summarized in Table 1.

In Example 1, a water-soluble, non-toxic liquid pressure-sensitive adhesive (#1-52G, Dyna-Tech Adhesives, Inc., Grafton, W. Va.) is directly coated onto 0.125 inch conductive polyurethane foam (Type 1, Conductance Materials, Inc., San Jose, Calif.) with a stainless steel spatula. The adhesive may also be applied to the foam by transfer-coating: a release paper (78# Clay Coated Kraft Silicone Coated One Side #8503, H. P. Smith, Div. of James River Corp., Bedford Park, Ill.), firmly anchored to a styrofoam base, has a small quantity of 1-52G adhesive applied to one end. The adhesive is allowed to become slightly tacky before using a glass rod to spread in one motion with uniform pressure. The results shown in Table 1 for Example 1 are from a direct-coated sample.

In Example 2, 1 part by weight of Shawinigan acetylene black (Chevron Chemical Co., Houston, Tex.) is added to 40 parts by weight of Dyna-Tech #1-52G. Acetylene black lumps must be removed before adding to adhesive, and shear during mixing is avoided by stirring with multiple thin rods. As soon as a uniform suspension is obtained, the foam (Type 1, Conductance Materials, Inc.) is direct-coated as in [1]. As shown in Table 1, this results in an improvement in contact impedance and initial DC offset voltage.

For Example 3, an emulsion of Gantrez S-95 (a vinyl ether polymer, from GAF Corp, Wayne, N.J.) and ethyl acetate (Fisher Scientific, Pittsburgh, Pa.) is made by mixing together equal parts by weight. Polymerization occurs when 2 parts by weight of Emulphogene BC-610 (a non-ionic surfactant, also from GAF Corp.) is added. One-tenth part acetylene black is blended in and the mixture is then blown partially dry to viscous consistency which allows either direct or transfer coating as in [1]. In Example 3, the composition is transfer-coated to 0.125 inch conductive polyurethane foam (LS-50, Keene Corp., Amesbury Mass.).

Example 4 is a sample manufactured using Adhesives Research, Inc. (Glen Rock, Pa.) Type 80-228-1 adhesive (formulation of which is a trade secret), laminated to 0.125 inch Conductance Materials Type 1 conductive polyurethane foam with the aid of a tissue substrate as depicted in FIGS. 1e and 1f.

The electrode pads described in the preceding examples were all subjected to actual ECG procedures and all demonstrated excellent signal detection when used in conjunction with the inventive lead amplifiers. When used with conventional passive lead wires, however, very poor to non-existent signal detection was evident.

TABLE 1

| Example | Impedance, ohms | DC Offset, mV 1 min. | DC Offset, mV 5 min. | AC Noise Baseline |
|---|---|---|---|---|
| 1 | 713,000 | −6 | 0 | <10 μV p-p |
| 2 | 490,000 | 0 | 0 | <10 μV p-p |
| 3 | 233,000 | 30 | 19 | <10 μV p-p |
| 4 | 258,000 | −13 | −5 | <10 μV p-p |

Further, the present invention also contemplates use of a conductive adhesive layer or substrate for skin-side contacting and an apertured insulative adhesive layer or substrate for contact-side contacting by the dry electrode pad, i.e., a hybrid of the adhesion teachings above presented. These adhesive layers can be discrete layers or coatings applied directly to the conductive foam pad or via tissue substrates as above described provided electrical continuity is maintained.

Further, the present invention contemplates use of both conductive and insulative (ie., non-conductive) adhesive on the same side of the pad in order to take advantage of the different adhesion characteristics which such adhesives may have. For example, one may apply an appropriate conductive adhesive layer directly to the skin-side of the conductive foam pad, and then apply further insulative adhesive exhibiting greater adhesiveness to selected portions of the skin-side of the pad and/or selected portions of the conductive adhesive. Once again, hybrid variations of the invention are possible.

FIG. 2 shows an embodiment of the connective lead wire 4 which electrically engages the conductive pad 2 and is adhesively contacted by the adhesive pad 3. Lead wire 4 includes a lead amplifier housing 5 which has a lead amplifier input contact 6. The lead amplifier input contact 6 is a solid conductive material that meets the same electrical stability requirements as the conductive pad and in combination with the pad maintains a total AC impedance to dry skin of not more than 1.5 million ohms at 10 Hz. An appropriate material is press-molded titanium hydride but it is understood that other materials meeting the above requirements are acceptable as well. Alternatively, any solid conductive material may be used for input contact 6 if the dry electrode pad 1 in use is resistant to fluids, and the total AC impedance of the pad and contact to dry skin is less than 1.5 million ohms (only pad in contact with skin). Part of input contact 6 may be a threaded section 31 (shown in FIG. 5) for mating with input connector 30. Alternatively, threaded section 31 may be deleted and input contact 6 affixed directly to input connector 30 by means of a conductive bonding agent such as silver cement. The amplifier housing 5 houses a lead amplifier circuit 10 discussed hereinafter and is made of an insulating material such as plastic or epoxy resin which is also impervious to fluids. A shielded cable 7 with four separate, insulated, internal conductors connects the output, ground, and power supply leads of the lead amplifier circuit 10 to a battery pack 8 and lead wire connector 9, which are shown in FIG. 2. In lieu of the battery pack 8 and connector 9, the lead amplifier circuit 10 may be connected directly to a monitor or other devices by means of a lead wire connector or permanently wired connection for providing supply current, ground and signal connections. The battery pack 8 supplies bipolar voltages of usually 1 to 3 volts and is encased in an insulating material such as plastic or epoxy. As shown in FIG. 2, the lead wire connector 9 is a miniature phone plug with the output signal and battery common (ground) connected to the plug. Other types of plugs may be used such as the standard pin plug, in which case there are two plugs at 9.

Figure 3:
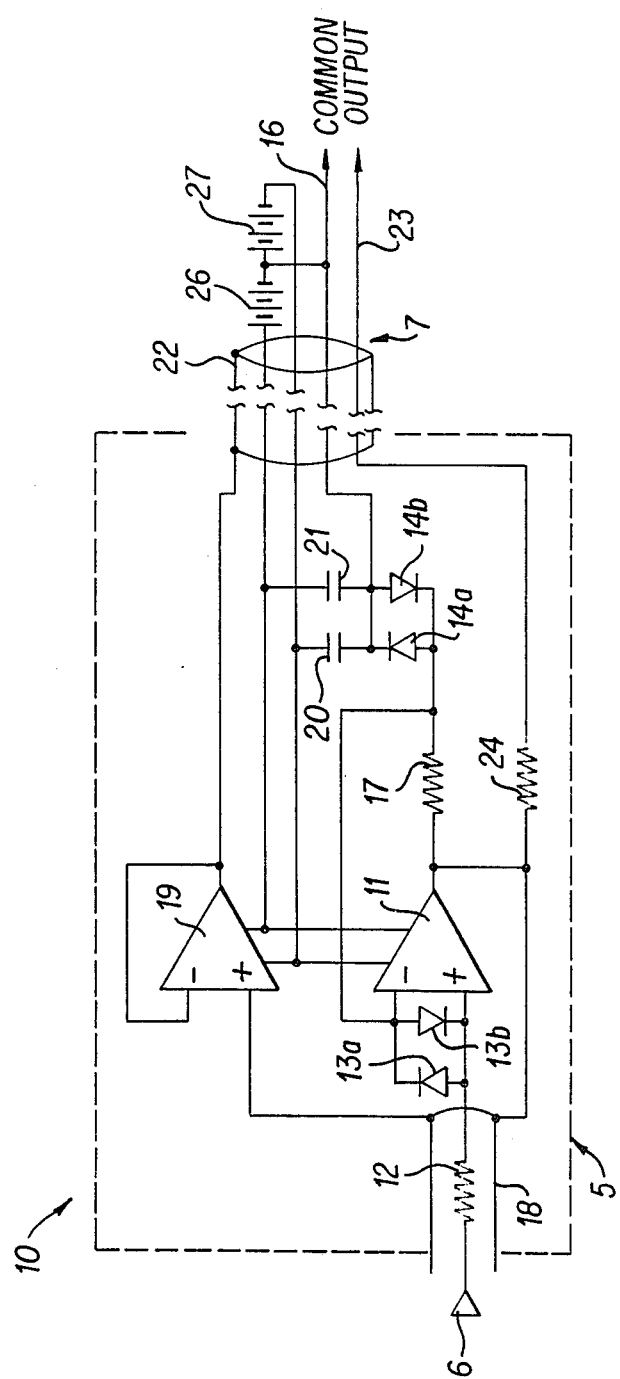
FIG. 3 is a circuit schematic of the lead wire amplifier according to the invention.

A circuit schematic of one embodiment of the lead amplifier circuit 10 is shown in FIG. 3. The insulating case 5 is represented by outer dotted-line and the conductive input contact 6 is shown at the edge of a voltage-driven shield 18 which is connected to the output of an operational amplifier 11 with noninverting unity gain. The input signal is conducted through resistor 12 which serves as a current limiter to prohibit fault currents above allowable limits from reaching the body. The inputs of amplifier 11 are protected from large amplitude voltages by signal diodes 13a, 13b, 14a and 14b, such as type 1N914, which shunt bipolar currents to battery common or ground 16 while preventing the voltage at the non-inverting input of amplifier 11 from rising to more than positive or negative 2 volts with respect to ground. Resistor 17, which may be 10,000 ohms, completes the feedback loop for amplifier 11 yet isolates its output from large currents that may flow in diodes 13a, 13b and 14a, 14b. A high input impedance into amplifier 11 of more than 10,000 megohms is maintained since diodes 13a and 13b have the same potential on both sides under normal operating conditions by virtue of the operational amplifier characterstics of amplifier 11. Furthermore, since the shield 18 is driven at the same potential as the input signal, any parasitic capacitance to ground through resistor 12 or connective input leads is minimized thus maintaining a measurably high input impedance and superior noise rejection characteristics of the lead wire amplifier circuit. Operational amplifier 19 is implemented in a unity gain, noninverting configuration in order to drive a lead wire shield 22 shielding the conductors of cable 7 at the same potential as that appearing on the output conductor 23, which results in improved shielding and lowered noise voltages generated by cable motion. It is understood that the outputs of amplifiers 11 and 19 may be nulled to zero offset by means of resistive connections (not shown) standard to the type of operational amplifiers used in the circuit, thereby maximizing the effects described above. Capacitors 20 and 21 are used in a common circuit technique to decouple the leads to the power supply batteries 26 and 27 from noise voltage sources, and resistor 24 isolates the output of 11 from the effects of capacitive loads.

Figure 4:
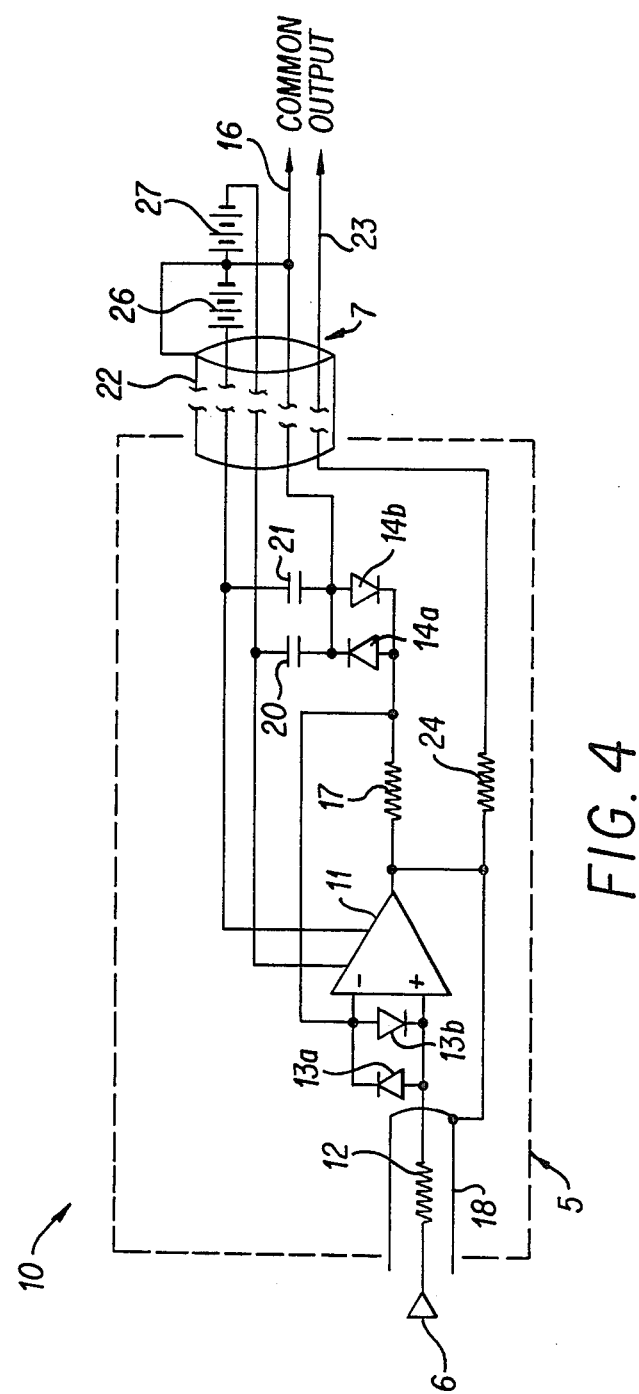
FIG. 4 is a circuit schematic of a minimum power lead amplifier according to the invention.

Another embodiment of the lead amplifier, shown in FIG. 4, dispenses with the shield driving amplifier 19 in order to minimize power supply requirements. The lead wire shield 22 in this example is connected to battery common 16 at the battery pack only, while the input contact shield is still voltage-driven by amplifier 11. Further reduction in power consumption can be realized by choosing low power integrated circuit amplifiers (such as CMOS types) exhibiting input offset voltages within a range of −3 mV to +3 mV and input bias currents of less than 50 pA.

An important feature in the circuit design of FIG. 4 resides in the input protection diodes 13a, 13b, 14a and 14b providing a pathway for sufficiently small bias currents from amplifier 11 when the input 6 is unconnected. Thus the output of amplifier 11 does not drift to one of the supply rails due to bias current charging the open input, and power consumption is limited to such a degree that it is no longer necessary to disconnect the batteries when the lead wire is not in use. Input impedance and open-input power consumption are directly related to the input offset voltage of operational amplifier 11; an input offset voltage range of −3 mV to +3 mV maintained without the aid of resistive nulling circuits has been shown to result in maximum input impedance while holding power consumption to a minimum. In low-power applications some CMOS operational amplifiers are not able to drive a signal into the capacitive load resulting from the grounded-shield cable configuration of FIG. 4. Therefore resistor 24 is important to the operation of the circuit in order to isolate the output of amplifier 11, and may be a 1% tolerance resistor of greater than 4000 ohms.

Alternative to the embodiments shown in FIGS. 3 and 4, the protective signal diode pairs 13a, 13b and 14a, 14b can be replaced with respective single Zener diode, i.e., each diode pair being replaced by a Zener diode. Any polarity orientation of the Zener diodes may be used. In order to obtain maximum protection for the operational amplifier 11 the Zener voltage should be less than 10 volts and preferably as small as possible. The use of the Zener diodes imposes a restraint on the value of input resistor 12; a resistance of not less than 1.5 megohms must be used in order to preserve the desired characteristics of the lead amplifier 11.

Since the Zener diodes serve the same function as the signal diode pairs in providing protection to the lead amplifier from large voltage transients, the advantage gained by their use is a reduction in the number of components of the lead amplifier. On the other hand, a disadvantage is apparent in the additional restraint imposed on the input resistor, whereas the signal diode pairs present no such restraint.

Details of the shielding and physical construction of an embodiment of the lead amplifier are shown in FIGS. 5a and 5b. A circuit board 28 with a circular guard ring 29 surrounding input resistor 12 is depicted in FIGS. 5a and 5b. Resistor 12 fits into a hole in circuit board 28, with one end soldered directly to the amplifier input trace on the component side of circuit board 28 and the opposite end soldered to input connector 30 which is threaded to accept the threaded section 31 of input contact 6. Alternatively, input connector 30 may be a solid conductive material with a protruding surface incorporating input contact 6 into a single piece. A metal tube 18 soldered to guard ring 29 and isolated from input connector 30 by insulative material 32 provides shielding for the extent of input connector 30. Guard ring 29 and hence shield 18 are connected to the output of amplifier 11 thus providing a voltage-driven input shield. The dual-in-line integrated circuit package 33 of amplifier 11 is positioned directly above resistor 12 in order to minimize the length of the input trace, and is soldered to traces on only the component side of circuit board board 28 without inserting the metal leads through holes in 28 so as to avoid accidental contact to the shielding.

Alternatively, as shown in FIGS. 5c and 5d, a surface mount integrated circuit package 33 containing amplifier 11 is positioned directly next to resistor 12 and diodes 13a and 13b in order to minimize the length of input trace 34. The input contact shield and circuit side guard ring remain the same as in FIG. 5b. By using surface mount components for most or all of the circuit elements of the lead wire amplifier as illustrated in FIGS. 5c and 5b, it is possible to greatly reduce the physical size of the lead wire amplifier while realizing an economical manufacturing process.

Figure 5E:
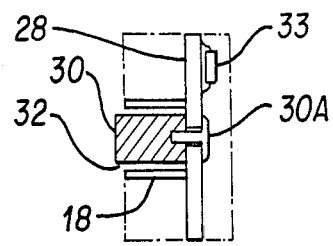
FIGS. 5e and 5f are respectively schematic side and plan views illustrating another embodiment of the lead amplifier and driven shield of the invention.
Figure 5F:
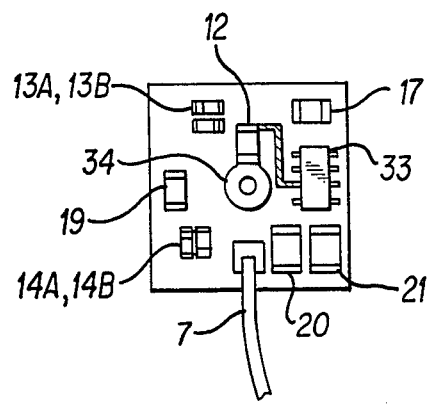

A further simplification in the manufacturing process is realized by replacing input resistor 12 with a small, flat surface mount resistor soldered to input trace 34 on top of circuit board 28, as shown in FIGS. 5e and 5f. The small size of the surface mount resistor 12 in combination with the guard ring construction 18 and 29 is sufficient to maintain the high input impedance of the lead amplifier. The attachment of the input contact is also considerably simplified, with screw 30a holding input contact 30 in place within guard ring or shield 18. Input contact 30 in this case does not need to be amenable to soldering, and can be any conductive material within the input contact restrictions. In particular, conductive silicone rubber of less than 100 ohm-cm resistivity is acceptable as an input contact for use with electrode pads coated with conductive adhesives, as long as the pads are resistant to fluids.

Furthermore, the shielding configuration of the invention as described above achieves superior shielding while eliminating the need for the bulky and potentially dangerous conductive shielding amplifier cases described in the prior art.

A ground or reference contact to the body is necessary to maintain a quiet stable signal and to provide a path for DC leakage currents. The ground or reference contact is a direct connection to the skin and is passive, i.e., it is made without the use of lead wire amplifiers. For patient safety the ground contact is usually connected to an isolated circuit common in the monitor amplifier instead of actual earth ground. For each dry electrode lead in contact with the body, lead common 16 is connected to both the body ground electrode and the isolated ground input of the monitor.

Figure 6C:
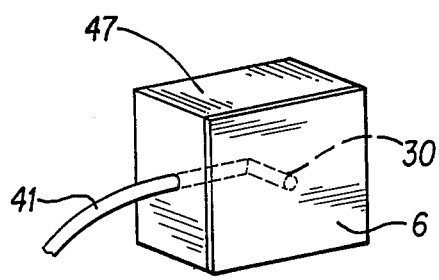
FIGS. 6a, 6b and 6c are perspective views of respective embodiments of the dry ground electrode, an elastic conductive strap and conductive foam pad, an adhesive pad and a small contact passive lead wire connector, and a conductive adhesive electrode pad and large-contact passive lead wire connector according to the invention.
Figure 6A:
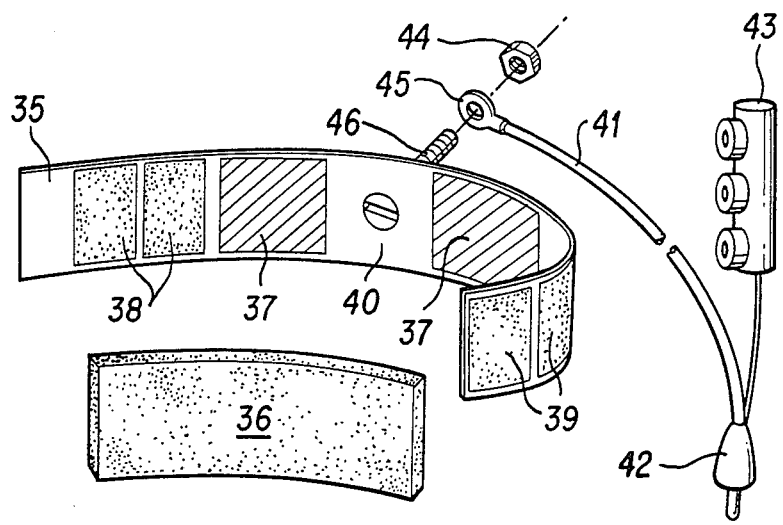
Figure 6B:
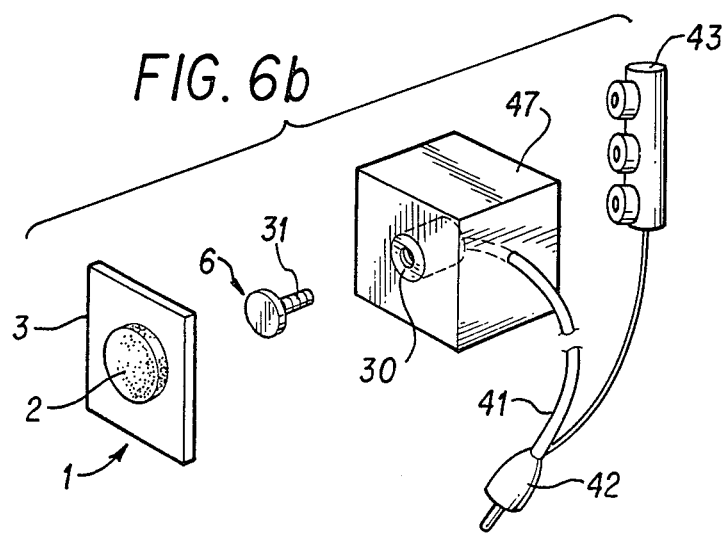

Two approaches as illustrated in FIGS. 6a and 6b are used according to the present invention to realize a stable dry ground electrode connection. In FIG. 6a, an adjustable elastic strap 35 is used to hold in contact with the skin of the arm or leg a strip of conductive pad 36 meeting the same specifications as described above for conductive electrode pads 2. Pad 36 makes electrical connection to the ground lead wire 41 via the conductive inside surface 37 of the elastic strap 35; the adjustable size of strap 35 is further extended through a connective system such as velcro hooks 39 and pads 38 in order to hold a snug but comfortable fit on any size arm or leg. The conductive surface 37 may be an elastic material interwoven with conductive metallic strands similar to devices used for the control of static charge accumulation on the body. However, surface 37 must remain isolated by pad 36 from direct contact to the skin in order to avoid noise voltages generated by sweat contamination. Lead wire 41 is held in contact to conductive material 37 by a conductive plate 40, screw 46 and nut 44, and connective eyelet 45. In the embodiment shown in FIG. 6a, a pin plug 42 and pin jacks 43 provide a connective means to the ground electrode input of a monitor and the lead wire common connectors from the common conductors 16 of lead wire cable 7, although it is understood that other types of connectors may be used.

An alternative ground electrode connection utilizing the dry electrode pad 1 is illustrated in FIG. 6b and employs the passive elements shown in the FIGS. 3 and 4, i.e., amplifiers and associated electrical components are deleted. The ground lead wire 41 connects to the body through the electrode pad 1 by means of an input contact 6 composed of conductive material as described above, with screw threads 31 mating to the threaded input connector 30. Alternatively, input connector 30 is a single conductive component incorporating contact 6, or else contact 6 without screw threads 31 may be attached to input connector 30 by a bonding agent such as silver cement. In both cases, lead wire 41 is connected directly to input connector 30, and the connective plug 42 and jacks 43 are the same as in the embodiment of FIG. 6a. In both embodiments of FIGS. 6a and 6b, ground lead wire 41 may be a shielded cable with the shield connected to ground at the monitor input.

A preferred embodiment of the ground electrode connector is shown in FIG. 6c. In this case, the input contact 6 covers the entire face of the insulative housing 47, and is comprised of a conductive material meeting the requirements for input contacts. This embodiment of the ground electrode is most appropriate for use with electrode pads of the type shown in FIG. 1g covered on both sides with a conductive adhesive, and therefore the preferred material for contact 6 is conductive silicone rubber of less than 100 ohm-cm resistivity. This material exhibits the best release without sticky residue from pressure-sensitive conductive adhesives while maintaining sufficient electrical contact. It is not acceptable for long-term monitoring unless the electrode pads are resistant to fluids. As shown in FIG. 6c, input contact 6 may be a thin layer of material laminated to insulative block 47, but it may also be as much as 95% or more of the total thickness of the entire ground connector, with the input connector 30 and ground lead wire 41 embedded within. Furthermore, input connector 30 may be expanded from the single rod shown in FIG. 6c to a sheet of conductive metallic material such as copper screening or aluminum foil, in order to increase the conductivity of the contact to 6. If the thickness of the input contact 6 exceeds 25% of the total thickness of the ground connector, an insulative extension of case 47 should cover the conductive areas for patient safety. As in FIGS. 6a and 6b, ground lead wire 41 may be a shielded cable with the shied and center conductor connected to (isolated) ground at the monitor input with plugs, jacks and hardwiring as appropriate.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A dry electrode system for the detection of biopotentials existing on the surface of the skin of a living body, comprising:
    a conductive dry electrode pad having opposed sides, one of which is adapted to contact said skin, comprising a resilient conductive pad having opposed sides, and adhesive means comprising first and second conductive adhesive layers applied to opposed sides of said conductive pad said first adhesive layer adapted to adhere said conductive pad to said skin; and
    an amplifying circuit connected to the other side of said dry electrode pad by means of said second adhesive layer for amplifying a biopotential transmitted via said dry electrode pad to said amplifying circuit.

2. A dry electrode system according to claim 1, wherein said conductive pad comprises a resilient material having not less than 5% rebound value, and wherein said dry electrode pad has an electrical impedance to dry skin of not greater than 1.5 million ohms at 10 Hz and an AC noise base line not greater than 150 $\mu$V peak (0.15 to 100 Hz) under conditions of dry to saturation within a 0.9% saline solution.

3. A dry electrode system according to claim 2, wherein said conductive pad comprises:
    an open-cell foam.

4. The dry electrode system as defined in claim 3, wherein said conductive foam pad comprises:
    carbon loaded polyurethane foam.

5. A dry electrode system according to claim 2, wherein said conductive pad comprises:
    a closed-cell foam.

6. A dry electrode system according to claim 5, wherein said conductive foam pad comprises:
    a cross-linked vinyl-nitrite polymer.

7. A dry electrode system according to claims 1, 2, 3 or 5 wherein said amplifying circuit comprises:
    an insulating housing having a conductive input contact mounted thereon and engaging the dry electrode pad,
    a lead amplifier having an input coupled to said input contact and an output, and
    a voltage driven first shield connected to said output of said lead amplifier and surrounding portions of said input contact not in engagement with said dry electrode pad.

8. The dry electrode system as defined in claim 7, wherein said conductive input contact comprises a material that maintains an AC noise voltage baseline of not more than 150 $\mu$V peak (0.15 to 100 Hz) under conditions ranging from dry to saturation with a 0.9% saline solution.

9. A dry electrode system according to claim 8, wherein said conductive input contact comprises:
    titanium hydride.

10. A dry electrode system according to claim 7, wherein said conductive input contact comprises:
    conductive silicone rubber.

11. A dry electrode system according to claim 7, wherein said amplifying circuit comprises:
said lead amplifier comprising an operational amplifier having inverting and non-inverting inputs,
first and second diodes connected in parallel inverse polarity across the inputs of said operational amplifier,
third and fourth diodes connected in parallel inverse polarity from the inverting input of said operational amplifier to a circuit common potential,
an output resistor connected from the inverting input to the output of said operational amplifier,
an input resistor connected between the non-inverting input of said operational amplifier and said conductive input contact, said input resistor at least partially contained within said voltage-driven first shield,
a lead wire cable having plural conductors connected to said lead amplifier and supplying power and common potential to said lead amplifier and taking out an output from said lead amplifier, and
a decoupling resistor connected from the output of said operational amplifier to an output conductor of the lead wire cable.

12. A dry electrode system according to claim 11, further comprising:
a circuit board having opposed sides, wherein on one of said sides of said circuit board said operational amplifier, said first through fourth diodes, and said output and decoupling resistors are mounted, said circuit board having an aperture through which said input resistor extends from the one side to the other side on which said conductive input contact is mounted.

13. A dry electrode system according to claim 12, wherein said lead wire cable comprises:
a flexible insulated multi-conductor cable including a pair of insulated conductors to carry bipolar supply currents to said lead amplifier, an insulated conductor to carry said circuit potential common current to and from said lead amplifier, said output conductor comprising an insulated conductor to carry an output signal from said lead amplifier, and a second shield shielding said insulated conductors.

14. A dry electrode system according to claim 13, wherein said amplifying circuit further comprises:
a voltage follower operational amplifier having a non-inverting input connected to the first shield, an inverting input connected to an output of said voltage follower operational amplifier and to said second shield.

15. A dry electrode system according to claim 13, wherein said second shield is connected to said insulated conductor carrying said circuit common potential.

16. A dry electrode system according to claim 13, comprising:
means for providing said circuit common potential, including,
an elastic ground strap having conductive portions and adapted to be mounted on a portion of the body,
a second resilient conductive pad contacting said conductive portions of said strap, and
a ground lead wire electrically conductively coupled between said second conductive pad and said insulated conductor carrying said circuit common potential.

17. A dry electrode system according to claim 13, comprising:
means for providing said circuit common potential, including,
a second dry electrode pad also comprising a resilient conductive pad having opposed sides one of which is adapted to engage the skin of the living body, and adhesive means having first and second adhesive surfaces, said first adhesive surface adapted to adhere said second conductive pad to the skin of said living body,
a second electrical contact mounted on a second housing and adhering to said second surface of said adhesive means, said second contact electrically contacting said second conductive pad, and
passive lead wire means for electrically conductively coupling said second electrical contact to said conductor carrying said circuit common potential.

18. A dry electrode system according to claim 17, comprising:
a conductive shield at least partially surrounding said second electrical contact.

19. A dry electrode system according to claims 1, 2, 3, or 5, wherein said amplifying circuit comprises:
an insulating housing having a conductive input contact mounted on said housing and engaging the dry electrode pad;
a lead amplifier having inverting and non-inverting inputs, one of which is coupled to said input contact, and an output;
first and second diodes connected in parallel inverse polarity across the inputs of said lead amplifier; and
third and fourth diodes connected in parallel inverse polarity from the inverting input of said lead amplifier to a circuit common potential.

20. A dry electrode system according to claim 19, comprising:
a voltage driven first shield connected to said output of said lead amplifier and surrounding portions of said input contact not in engagement with said pad.

21. The dry electrode system as defined in claim 19, wherein said conductive input contact comprises a material that maintains an AC noise voltage baseline of not more than 150 $\mu$V peak (0.15 to 100 Hz) under conditions ranging from dry to saturation with 0.9% saline solution.

22. A dry electrode system according to claim 21, wherein said conductive input contact comprises titanium hydride.

23. A dry electrode system according to claim 19, wherein said conductive input contact comprises:
conductive silicone rubber.

24. A dry electrode system according to claim 1, 2, 3 or 5, wherein said adhesive means comprises:
a pair of tissue substrates each having opposed sides covered with a conductive adhesive layer, said pair of substrates sandwiching said resilient conductive pad therebetween.

25. A dry electrode system according to claim 7, wherein said adhesive means comprises:
a pair of tissue substrates each having opposed sides covered with a conductive adhesive layer, said pair of substrates sandwiching said resilient conductive pad therebetween.

26. A dry electrode system according to claim 19, wherein said adhesive means comprises:
a pair of tissue substrates each having opposed sides covered with a conductive adhesive layer, said pair of substrates sandwiching said resilient conductive pad therebetween.

27. A dry electrode system according to claim 20, wherein said adhesive means comprises:
a pair of tissue substrates each having opposed sides covered with a conductive adhesive layer, said pair of substrates sandwiching said resilient conductive pad therebetween.

28. A dry electrode system according to claims 1, 2, 3 or 5 wherein:
said first adhesive layer comprises a hypoallergenic adhesive material, and
said second adhesive layer comprises an adhesive material which leaves no adhesive residue on said amplifying circuit after removal therefrom.

29. A dry electrode system according to claim 7, wherein:
said first adhesive layer comprises a hypoallergenic adhesive material, and
said second adhesive layer comprises an adhesive material which leaves no adhesive residue on said amplifying circuit after removal therefrom.

30. A dry electrode system according to claim 19, wherein:
said first adhesive layer comprises a hypoallergenic adhesive material, and
said second adhesive layer comprises an adhesive material which leaves no adhesive residue on said amplifying circuit after removal therefrom.

31. A dry electrode system according to claim 20, wherein:
said first adhesive layer comprises a hypoallergenic adhesive material, and
said second adhesive layer comprises an adhesive material which leaves no adhesive residue on said amplifying circuit after removal therefrom.

32. A dry electrode system according to claim 24 wherein:
said first adhesive layer comprises a hypoallergenic adhesive material, and
said second adhesive layer comprises an adhesive material which leaves no adhesive residue on said amplifying circuit after removal therefrom.

33. A dry electrode system according to claim 7, wherein said conductive pad comprises:
a flexible conductive film provided on at least one side of said resilient conductive pad, said conductive film having an electrical impedance to dry skin of not greater than 1.5 million ohms at 10 Hz and maintaining an AC noise voltage (0.15 to 100 Hz) of not more than 150 $\mu$V peak under conditions ranging from dry to saturation with a 0.9% saline solution.

34. A dry electrode system according to claim 19, wherein said conductive pad comprises:
a flexible conductive film provided on at least one side of said resilient conductive pad, said conductive film having an electrical impedance to dry skin of not greater than 1.5 million ohms at 10 Hz and maintaining an AC noise voltage (0.15 to 100 Hz) of not more than 150 $\mu$V peak under conditions ranging from dry to saturation with a 0.9% saline solution.

35. A dry electrode system according to claim 20, wherein said conductive pad comprises:
a flexible conductive film provided on at least one side of said resilient conductive pad, said conductive film having an electrical impedance to dry skin of not greater than 1.5 million ohms at 10 Hz and maintaining an AC noise voltage (0.15 to 100 Hz) of not more than 150 $\mu$V peak under conditions ranging from dry to saturation with a 0.9% saline solution.

36. A dry electrode system according to claim 24, wherein said conductive pad comprises:
a flexible conductive film provided on at least one side of said resilient conductive pad, said conductive film having an electrical impedance to dry skin of not greater than 1.5 million ohms at 10 Hz and maintaining an AC noise voltage (0.15 to 100 Hz) of not more than 150 $\mu$V peak under conditions ranging from dry to saturation with a 0.9% saline solution.

37. A dry electrode system for the detection of biopotentials existing on the surface of the skin of a living body, comprising:
a conductive dry electrode pad comprising a resilient conductive pad and having opposed sides, one of which is adapted to contact the skin of said living body, and adhesive means, having first and second adhesive layers, at least said first adhesive layer being conductive and adapted to adhere said conductive pad to said skin; and
an amplifying circuit connected to the other side of said dry electrode pad for amplifying a biopotential transmitted via said dry electrode pad to said amplifying circuit;
wherein said adhesive means comprises:
said conductive first adhesive layer applied to said one side of said resilient conductive pad, and
said second adhesive layer being an insulative adhesive layer applied to selected portions of the other side of said resilient conductive pad, said conductive first adhesive layer adapted to adhesively engage the skin and said insulative second adhesive layer adhesively engaging the amplifying circuit with said resilient conductive pad in contact with said amplifying circuit.

38. A dry electrode system according to claim 37, wherein:
said conductive adhesive layer comprises a hypoallergenic adhesive material, and
said insulative adhesive layer comprises an adhesive material which leaves no adhesive residue on said amplifying circuit after removal therefrom.

39. A dry electrode system according to claim 1, 2, 3, 5 or 37, wherein said conductive pad comprises:
a flexible conductive film provided on at least one side of said resilient conductive pad, said conductive film having an electrical impedance to dry skin of not greater than 1.5 million ohms at 10 Hz and maintaining an AC noise voltage (0.15 to 100 Hz) of not more than 150 $\mu$V peak under conditions ranging from dry to saturation with a 0.9% saline solution.

40. A dry electrode system according to claim 39, wherein said conductive film is provided on both opposed sides of said resilient conductive pad.

41. A dry electrode system according to claim 40, wherein said conductive film comprises:
a cured mixture of one and one half parts by volume graphite powder, five parts by volume distilled water and ten parts by volume of liquid latex.

42. A dry electrode system according to claim 37, wherein said amplifying circuit comprises:

an insulating housing having a conductive input contact mounted thereon engaging the dry electrode pad, a lead amplifier having an input coupled to said input contact and an output, and a voltage driven first shield connected to said output of said lead amplifier and surrounding portions of said input contact not in engagement with said dry electrode pad.

43. The dry electrode system as defined in claim 42, wherein said conductive input contact comprises a material that maintains an AC noise voltage baseline of not more than 150 $\mu$V peak (0.15 to 100 Hz) under conditions ranging from dry to saturation with a 0.9% saline solution.

44. A dry electrode system according to claim 43, wherein said conductive input contact comprises:
titanium hydride.

45. A dry electrode system according to claim 42, wherein said conductive input contact comprises:
conductive silicone rubber.

46. A dry electrode system according to claim 42, wherein said amplifying circuit comprises:
said lead amplifier comprising an operational amplifier having inverting and non-inverting inputs,
first and second diodes connected in parallel inverse polarity across the inputs of said operational amplifier,
third and fourth diodes connected in parallel inverse poarlity from the inverting input of said operational amplifier to a circuit common potential,
an output resistor connected from the inverting input to the output of said operational amplifier,
an input resistor connected between the noninverting input of said operational amplifier and said conductive input contact, said input resistor at least partially contained within said voltage-driven first shield,
a lead wire cable having plural conductors connected to said lead amplifier and supplying power and common potential to said lead amplifier and taking out an output from said lead amplifier, and
a decoupling resistor connected from the output of said operational amplifier to an output conductor of the lead wire cable.

47. A dry electrode system according to claim 46, further comprising:
a circuit board having opposed sides, wherein on one of said sides of said circuit board said operational amplifier, said first through fourth diodes, and said output and decoupling resistors are mounted, said circuit board having an aperture through which said input resistor extends from the one side to the other side on which said conductive input contact is mounted.

48. A dry electrode system according to claim 47, wherein said lead wire cable comprises:
a flexible insulated multi-conductor cable including a pair of insulated conductors to carry bipolar supply currents to said lead amplifier, an insulated conductor to carry said circuit potential common current to and from said lead amplifier, said output conductor comprising an insulated conductor to carry an output signal from said lead amplifier, and a second shield shielding said insulated conductors.

49. A dry electrode system according to claim 48, wherein said amplifying circuit further comprises:

a voltage follower operational amplifier having a non-inverting input connected to the first shield, and an inverting input connected to an output of said voltage follower operational amplifier and to said second shield.

50. A dry electrode system according to claim 48, wherein said second shield is connected to said insulated conductor carrying said circuit common potential.

51. A dry electrode system according to claim 48, comprising:
means for providing said circuit common potential, including,
an elastic ground strap having conductive portions and adapted to be mounted on a portion of the body,
a second resilient conductive pad contacting said conductive portions of said strap, and
a ground lead wire electrically conductively coupled between said second conductive pad and said insulated conductor carrying said circuit common potential.

52. A dry electrode system according to claim 48, comprising:
means for providing said circuit common potential, including,
a second dry electrode pad also comprising a resilient conductive pad having opposed sides one of which is adapted to engage the skin of the living body, and adhesive means having first and second adhesive surfaces, said first adhesive surface adapted to adhere said second conductive pad to the skin of said living body,
a second electrical contact mounted on a second housing and adhering to said second surface of said adhesive means, said second contact electrically contacting said second conductive pad, and
passive lead wire means for electrically conductively coupling said second electrical contact to said conductor carrying said circuit common potential.

53. A dry electrode system according to claim 82, comprising:
a conductive shield at least partially surrounding said second electrical contact.

54. A dry electrode system according to claim 37, wherein said amplifying circuit comprises:
an insulating housing having a conductive input contact mounted on said housing and engaging the dry electrode pad;
a lead amplifier having inverting and noninverting inputs, one of which is coupled to said input contact, and an output;
first and second diodes connected in parallel inverse polarity across the inputs of said lead amplifier; and
third and fourth diodes connected in parallel inverse polarity from the inverting input of said lead amplifier to a circuit common potential.

55. A dry electrode system according to claim 54, comprising:
a voltage driven first shield connected to said output of said lead amplifier and surrounding portions of said input contact not in engagement with said pad.

56. The dry electrode system as defined in claim 54, wherein said conductive input contact comprises a material that maintains an AC noise voltage baseline of not more than 150 $\mu$V peak (0.15 to 100 Hz) under conditions ranging from dry to saturation with 0.9% saline solution.

57. A dry electrode system according to claim 56, wherein said conductive input contact comprises titanium hydride.

58. A dry electrode system according to claim 54, wherein said conductive input contact comprises:
 conductive silicone rubber.

59. A dry electrode system for the detection of biopotentials existing on the surface of the skin of a living body, comprising:
 a conductive dry electrode pad comprising a resilient conductive pad and having opposed sides, one of which is adapted to contact the skin of said living body, and adhesive means, having first and second adhesive surfaces, at least said first adhesive surface being conductive and adapted to adhere said conductive pad to said skin; and
 an amplifying circuit connected to the other side of said dry electrode pad for amplifying a biopotential transmitted via said dry electrode pad to said amplifying circuit;
 wherein said adhesive means comprises:
  a conductive adhesive layer applied to at least a portion of said resilient conductive pad; and
  an insulative adhesive layer applied to a selected portion of at least one of the resilient conductive pad and the adhesive conductive layer.

60. A dry electrode pad for enabling electrical and mechanical connection between the skin of a living body and an amplifying circuit electrically coupled to a monitor, comprising:
 a resilient conductive pad having first and second opposed sides, one of which is adapted to contact the skin of said living body; and
 adhesive means having opposed first and second adhesive surfaces respectively provided on the opposed sides of said conductive pad, said first adhesive surface being conductive and adapted to adhere to the skin such that one opposed side of said conductive pad is in electrical connection with the skin, said second adhesive surface adapted to adhesively engage said amplifying circuit with the other opposed side of said conductive pad in electrical connection with said amplifying circuit.

61. A dry electrode pad according to claim 60, wherein said conductive pad comprises a resilient material having not less than 5% rebound value, and wherein said dry electrode pad has an electrical impedance to dry skin of not greater than 1.5 million ohms at 10 Hz and an AC noise base line not greater than 150 μV peak (0.15 to 100 Hz) under conditions of dry to saturation within a 0.9% saline solution.

62. A dry electrode pad according to claim 61, wherein said conductive pad comprises:
 an open-cell foam.

63. The dry electrode pad as defined in claim 62, wherein said conductive foam pad comprises:
 carbon loaded polyurethane foam.

64. A dry electrode pad according to claim 61, wherein said conductive pad comprises:
 a closed-cell foam.

65. A dry electrode pad according to claim 64, wherein said conductive foam pad comprises:
 a cross-linked vinyl-nitrite polymer.

66. A dry electrode pad according to claims 60, 61, 62 or 64, wherein said adhesive means comprises:
 first and second conductive adhesive layers applied to respective opposed sides of said resilient conductive foam pad.

67. A dry electrode pad according to claims 60, 61, 62 or 64, wherein said adhesive means comprises:
 a pair of tissue substrates each having opposed sides covered with a conductive adhesive layer, said pair of substrates sandwiching said resilient conductive pad therebetween.

68. A dry electrode pad according to claims 60, 61, 62 or 64, wherein said adhesive means comprises:
 a conductive adhesive layer applied to said one side of said resilient conductive pad and an insulative adhesive applied to selected portions of the other side of said resilient conductive pad, said conductive adhesive adapted to adhesively engage the skin, and said insulative adhesive layer adapted to adhesively engage the amplifying circuit with said resilient conductive pad in electrical connection with said amplifying circuit.

69. A dry electrode pad according to claims 60, 61, 62 or 64, wherein:
 said first adhesive surface comprises a hypoallergenic adhesive material, and
 said second adhesive surface comprises an adhesive material which leaves no adhesive residue on said amplifying circuit after removal therefrom.

70. A dry electrode pad according to claims 60, 61, 62 or 64, wherein said conductive pad comprises:
 a flexible conductive film provided on at least one side of said conductive foam pad, said conductive film having an electrical impedance to dry skin of not greater than 1.5 million ohms at 10 Hz and maintaining an AC noise voltage (0.15 to 100 Hz) of not more than 150 μV peak under conditions ranging from dry to saturation with a 0.9% saline solution.

71. A dry electrode pad according to claim 70, wherein said conductive film is provided on both opposed sides of said conductive pad.

72. A dry electrode pad according to claim 71, wherein said conductive film comprising:
 a cured mixture of one and one half parts by volume graphite powder, five parts by volume distilled water and ten parts by volume of liquid latex.

73. A dry electrode pad according to claims 57, 61, 62 or 64, wherein said adhesive means comprises:
 a conductive adhesive layer applied to at least a portion of said resilient conductive pad; and
 an insulative adhesive layer applied to a selected portion of at least one of the resilient conductive pad and the conductive adhesive layer.

74. A dry electrode pad according to claims 60, 61, 62 or 64, wherein said adhesive means comprises:
 a conductive adhesive layer applied to at least a portion of said resilient conductive pad; and
 an insulative adhesive layer applied to a selected portion of at least one of the resilient conductive pad and the conductive adhesive layer.

* * * * *